United States Patent [19]
Tropiano

[11] Patent Number: 5,607,424
[45] Date of Patent: Mar. 4, 1997

[54] DOMED CAGE

[76] Inventor: Patrick Tropiano, 550, rue Paradis, Batiment Cl, 13 008 Marseille, France

[21] Appl. No.: 420,722

[22] Filed: Apr. 10, 1995

[51] Int. Cl.⁶ .................................................. A61B 17/56
[52] U.S. Cl. .............................................. 606/61; 606/17
[58] Field of Search ........................... 606/61, 60; 623/17

[56] References Cited

U.S. PATENT DOCUMENTS

| | | | |
|---|---|---|---|
| 4,932,969 | 6/1990 | Frey et al. | 623/17 |
| 5,192,327 | 3/1993 | Brantigan | 623/17 |
| 5,458,638 | 10/1995 | Kuslich et al. | 623/17 |

Primary Examiner—Michael Powell Buiz
Assistant Examiner—Mark S. Leonardo
Attorney, Agent, or Firm—John J. Byrne

[57] ABSTRACT

A cage for use in a spinal repair system wherein a pair of inert, relatively open bone-graft contouring cages are disposed between adjacent vertebrae mounted to the boney structure of these vertebrae wherein the vertebrae will knit together and act as a single unit. The upper and lower surfaces of the cages follow an arcuate path for increased contact with the abutting surfaces of the vertebrae themselves.

2 Claims, 1 Drawing Sheet

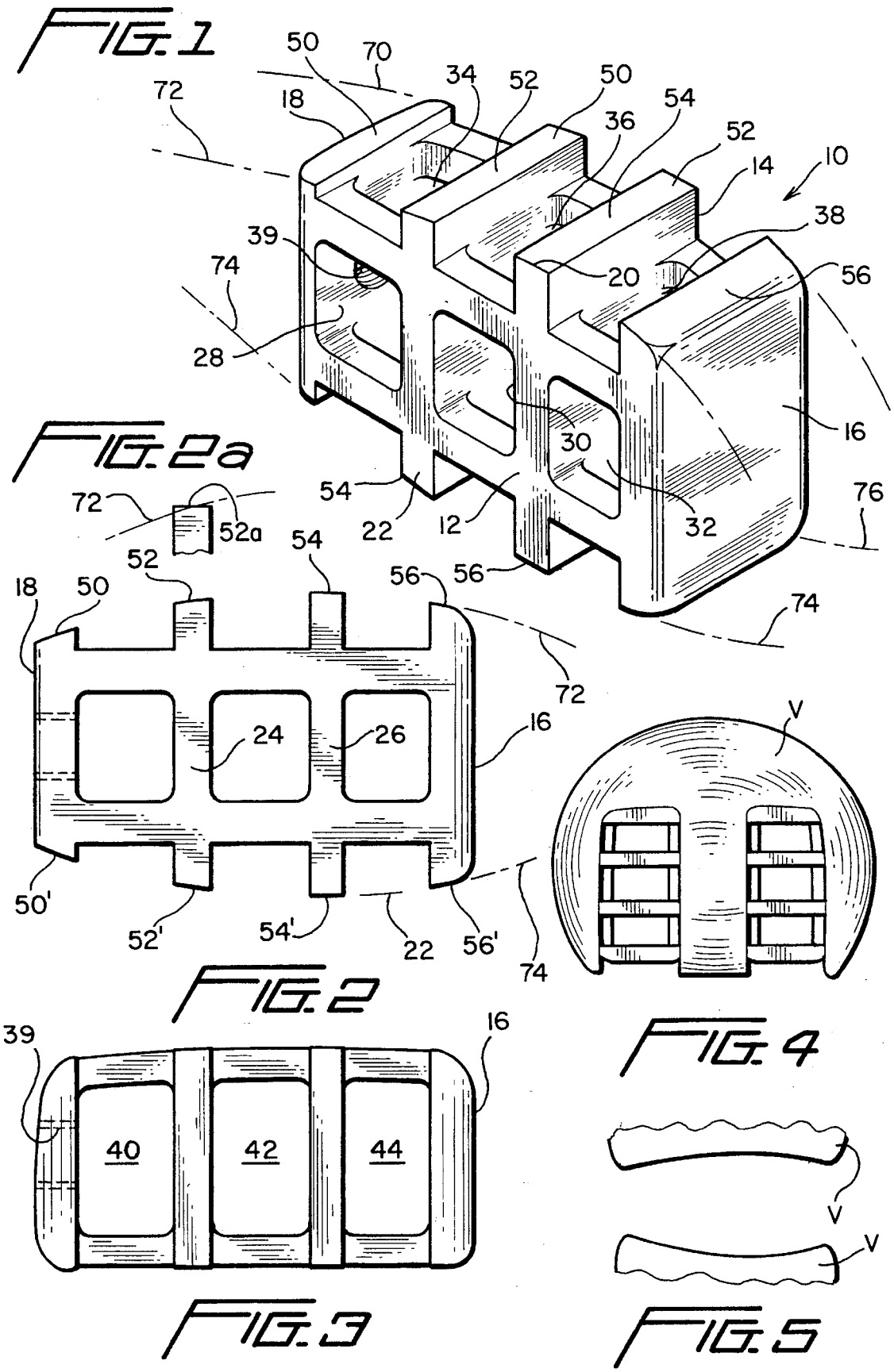

DOMED CAGE

BACKGROUND OF THE INVENTION

One of the most troublesome and painful dysfunctions of the human body relates to the complicated but essential construction of the spinal column. As those skilled in the art, we are aware that the spinal column is comprised of a series of vertebrae that have flexible discs therebetween and an outgrowth of bones that include the dorsal and pedicle that serve, together with the vertebrae, to protect the spinal cord and, at the same time, provide spinal flexibility through slidable engagement with one another.

These bone elements also provide openings through which various nerves and vessels can extend. When something goes wrong with the spinal functions, the openings often pinch the nerve extending therethrough, causing a great deal of pain. One of the most common dysfunctions in the back is the rupture or a displacement of a disc between the vertebra. Modern medicine and science has not found a suitable disc replacement. Therefore, many spinal pains can be reduced or eliminated by fusing the adjacent vertebrae on either side of the injured disc. Although such a fusing reduces the degree of flexibility in the spinal column, such fusion is often the best medical procedure available for this condition. This invention relates generally to a cage apparatus that has arcuate upper and lower surfaces for enhancing the medical procedure with which it is used.

FIELD OF THE INVENTION

One of the most costly health problems to society today involves back pain and pathology of the spine. This sometimes devastating pathology can affect individuals at all stages in life and pull them from an active life at a relatively young age. Therefore, this pathology not only causes great suffering to the victims, it is also a burden to society which must provide for those who are removed from active life for decades. Thus, the cost of this pathology to society as a whole is considered to be in the billions of dollars each year.

The spine is composed of bony vertebra with flexible discs therebetween in a resulting structure referred to as the vertebral column. Because of its structure, it is capable of flexing and extending like a chain. Each vertebrae is composed of a body having two relatively large flat oblique-shaped surfaces into which the disc is attached. Extending out of the posterior aspect of the vertebral body are two tube like structures called the pedicels and attached to the pedicles are the lamina, facet joints and various processes referred to as the posterior elements. Together, two vertebrae with a disc and associated ligaments are called a vertebral motion segment. Therefore, an intact vertebral column is composed of several motion segments which are each composed of their corresponding vertebral bony, disc and ligamentous structures. Combined, this structure functions as protection of the spinal cord, bears the load of the body and can bend. An intact vertebral column, with all of its posterior bony and soft tissue components, for a vertebral canal through which the spinal cord and its existing roots, as well as the vascular structures, may pass. The vertebral canal is divided into subdivisions which are of great important to the spine surgeon treating ailments because it is often here the pain generating pathology is found and the ailment is treated.

The spine is subject to many pathologic and pain generating changes which can occur in the disc, the posterior elements, and finally the vertebral body. These can be caused by congenital deformities, traumatic injuries, degenerative changes at one or several motion segments at a time. Such changes can cause painful excessive motion, or collapse of a motion segment which contracts the spinal canal and compresses the neural structures to cause debilitating pain, paralysis, or both, which can cause nerve root compression, spinal stenosis, or excessive mobility which can be the source of severe pain. This can happen in one or several motion segments at the same time.

For the surgeon treating this pathology, the ideal goal is to restore to degenerative motion segment and its spinal canal to their normal spatial relationship while assuring their normal functional movement and weight bearing capabilities. Unfortunately, no successful prothesis exist that satisfactorily replace the form and function of the disc, posterior elements and the vertebral body. The state of the art treatment remains an arthrodesis which means the fusion of 2 or more vertebral bodies of a motion segment together to make one solid bony segment. In the treatment described within the realm of this invention, the procedure with our invention can restore all of the normal functions except motion. That is, the surgeon can restore normal spatial relation between two vertebral bodies, assuring proper spinal alignment and balance, as well as restore the necessary openings for the neural and vascular structures to pass. Since the vertebrae are fused into one bone, painful motion is eliminated as well.

Since a spine is composed of many motion segments, even with one segment fused for the relief of pain, the patient movement is minimally restricted in a manner that allows them to live a normal life. The current invention improves the reliability and precision of this procedure.

The present invention relates to the surgical correction of spinal columns by fusion between adjacent vertebrae of a damaged disc. The invention provides specifically for unique, durable, cages that, although having considerable compressive strength, are open enough to contain a large amount of bone graft. The invention also relates to an arcuate structure that will stabilize the adjacent vertebrae. This structure will cause these generally concave surfaces to better mate with the generally convex surfaces of the adjacent vertebral surfaces.

An objective of this invention is to provide an improved spinal support fixation and methodology which provide stability between adjacent vertebrae and the shape will help the cages stay in place.

Another objective of the present invention is to provide apparatus which will aid in fixing appropriate elements in place until bone fusion occurs.

Another very important objective of the invention is to provide cages that have arcuate upper and lower surfaces, most of which are formed with large openings so that maximum bone graft material can be received and placed in contact with graft material outside the cage.

A further objective of this invention is to provide unique cages for the fusion techniques involved which are entirely adaptable for use with the tooling with which physicians are currently skilled.

Other objectives and advantages of this invention will be more apparent upon a reading of the following specification take together with the drawings.

DISCUSSION OF THE PRIOR ART IN THE FIELD OF THIS INVENTION

A good understanding of the cage-type fusion methodology can be obtained from Brantigan U.S. Pat. Nos. 4,743, 256, 4,834,757 and 4,878,915; and in the co-pending application of Robert B. Lange, Jr., Ser. No. 08/235,943, filed May 2, 1994, now abandoned, my colleague. The Brantigan cages are of a type which this invention improves by providing an arcuate exterior surface and with adequate space bone graft material.

Other advantages and features of the present invention will be apparent to those skilled in the art after reading the following specification with reference to the accompanying drawings.

BRIEF DESCRIPTION OF THE DRAWINGS

FIG. 1 is a perspective view of the cage of this invention;

FIG. 2 is a side elevation;

FIG. 2a is an embodiment of the upper and lower surface edges;

FIG. 3 is a top plan view of the cage as seen in FIG. 1;

FIG. 4 is a diagrammatic plan showing the location of the cages with respect to the vertebrae; and FIG. 5 is a diagrammatic elevation showing the generally convex shapes, somewhat exaggerated, of the vertebrae surfaces.

DESCRIPTION OF THE PREFERRED EMBODIMENTS

Referring now to the drawings wherein like elements indicate like parts, the cage of this invention is depicted by the numeral 10. The cage 10 has a pair of side surfaces 12 and 14, a front surface 16, and a rear or posterior surface 18. The cage is completed by having a top 20 and a bottom 22.

Intermediate the length of cage 10 are a pair of interior struts 24 and 26, which extend between sides 12 and 14 and engage the solid part of walls between the side openings. Side 12 has openings 28, 30 and 32, and side 14 has openings 34, 36 and 38. Surface 18 has a threaded opening 39 to receive a positioning tool of a type well-known to those skilled in the art. Partitions or struts 24 and 26 divide the cage 10 into three compartments; namely, 40, 42 and 44. Note the smooth front surface of 16 and the other side walls. This provides surfaces which will not tear or mangle the delicate nerves and blood vessels near the site of the spinal cord.

The upper edges 50, 52, 54 and 56 of the walls 16 and 18, and the struts 24 and 26 follow the curvilinear path defined by arcs 70 and 72. The lower edges thereof 50', 52', 54' and 56' follow the curvilinear path defined by the arcs 74 and 76. In combination they form dome-like surfaces for the cage. These dome-like surfaces mate to some extent with the surfaces of the adjacent vertebrae. See FIG. 5. This is the essence of the improvement.

Note the imaginary arcuate lines 70, 72, 74 and 76. They are used to depict the front to rear dome-like shape of the cages along the upper and lower surfaces. Although the upper and lower edges of the struts are flat, they are in the curvilinear path so depicted.

As seen in FIGS. 1 and 2, the upper and lower surfaces fall directly in the path of the arcuate planes defined by 70–72 and 74–76, respectively. Note how the surfaces slant where necessary. As seen in FIG. 2a, the surfaces 50, 52, 54, 56, 50', 52', 54' and 56' can also be flat with respect to the longitudinal axis of the cage but yet, as a group, fall in the arcuate planes.

From the foregoing specification, it will be understood by those skilled in the art that this structure provides important contributions to spinal correction procedures by providing a synergism of elements between structure and bone that will permit the vertebrae to be knitted together with a balance and with a naturalness.

The embodiment disclosed is the invention as presently contemplated. However, the reader should understand that various changes and modifications can be made without departing from the spirit of the present invention as described in the following claim.

I claim:

1. In a spinal column where adjacent vertebrae have first and second opposed faces defining a space from which a disc has been removed, a device for replacing said disc comprising:

a pair of inert cages each cage comprised of;
first and second side walls respectively having first and second upper surfaces and first and second lower surfaces,
a bottom surface extending between said first and second lower surfaces,
a top surface extending between said first and second upper surfaces,
an anterior plate at one end of said cage, and
a posterior plate at the other end of said cage;
said anterior and posterior plates being substantially solid except for a threaded opening in said posterior plate;
a series of strut plates extending between said first and second side walls each of which have top and bottom edges and wherein said top edges form a portion of said top surface and wherein said bottom edges form a portion of said bottom surface;
said bottom surface and bottom edges from forming an arcuate dome; and,
said top surface and top edges forming a second arcuate dome.

2. The cages of claim 1 wherein said domes are configured to follow the contours of their adjacent vertebrae surfaces.

* * * * *